United States Patent [19]
Bailey

[11] Patent Number: 5,807,748
[45] Date of Patent: Sep. 15, 1998

[54] N-TERMINAL PROTEIN SEQUENCING REAGENTS AND METHODS WHICH FORM AMINO ACID DETECTABLE BY A VARIETY OF TECHNIQUES

[75] Inventor: Jerome Bailey, Sunnyvale, Calif.

[73] Assignee: City of Hope, Duarte, Calif.

[21] Appl. No.: 765,398

[22] PCT Filed: Jul. 8, 1994

[86] PCT No.: PCT/US94/07785

§ 371 Date: Apr. 11, 1997

§ 102(e) Date: Apr. 11, 1997

[87] PCT Pub. No.: WO96/02003

PCT Pub. Date: Jan. 25, 1996

[51] Int. Cl.$^6$ .......................... G01N 33/68; C07D 235/04
[52] U.S. Cl. .......................... 436/89; 436/172; 436/173; 530/341; 530/410; 548/333.5; 548/334.1
[58] Field of Search .................. 436/89, 172, 173; 530/341, 402, 410; 548/333.5, 334.1

[56] References Cited

U.S. PATENT DOCUMENTS

| | | | |
|---|---|---|---|
| 5,008,205 | 4/1991 | Horn | 436/89 |
| 5,246,865 | 9/1993 | Stolowitz | 436/89 |

*Primary Examiner*—David A. Redding
*Attorney, Agent, or Firm*—Rothwell, Figg, Ernst & Kurz

[57] ABSTRACT

Novel alkoxythiocarbonylimidazoles provide new reagents for the N-terminal sequencing of small polypeptide samples. These reagents form an alkoxy thiourea derivative which is cleaved with acid to remove the N-terminal amino acid as a stable thiazolinone which does not rearrange to a thiohydantoin. This thiazolinone may be derivatized to provide a detectable group such as a fluorescent group or ionizable group detectable by mass spectrometry.

16 Claims, 14 Drawing Sheets

Methoxythiazolinone (MTZ)

Derivatized N-Terminal Amino Acid

N-TERMINAL PROTEIN SEQUENCING REAGENTS AND METHODS WHICH FORM AMINO ACID DETECTABLE BY A VARIETY OF TECHNIQUES

This invention was made with government support under Grant No. GM46022 awarded by the National Institutes of Health, General Medicine. The government has certain rights in the invention.

FIELD OF THE INVENTION

This invention relates to the sequential degradation of proteins and peptides from the N-terminus. More particularly, the invention relates to the sequential N-terminal degradation of small peptide samples. Sequencing sensitivity is enhanced by removal of the peptide N-terminal amino acid as a thiazolinone derivative which is derivatized by a nucleophile containing a fluorescent group or a functional group appropriate for a particular method of detection.

BACKGROUND OF THE INVENTION

One of the primary goals of protein chemists is to relate the function of a protein to its structure. With this goal in mind, an early step in the structural characterization of proteins is the determination of primary structure or sequence. Currently, primary structural determination can be accomplished either by sequencing the protein on an automated sequencer using the Edman chemistry for successive degradation or by sequencing the gene for that protein using established DNA sequencing methodology. Although protein sequencing can be considered to be more difficult and slower than DNA sequencing, it often provides information not obtainable by the latter method. Protein sequencing can provide information concerning posttranslational modifications which are not predictable from the gene sequence, such as location of proteolytic cleavage sites. Furthermore, it is a key method for the determination of protein sequence information which can be used for the design of oligonucleotide probes complementary to predicted gene sequences. In many cases, these oligonucleotide probes, obtained from protein sequence analysis, have been the only route to the cloning of a particular gene.

Currently, protein sequence analysis is primarily accomplished with the use of an automated sequencer using chemistry developed by Edman over 40 years ago (1)[1] (FIG. 1). Since that time improvement in the instrumentation (2,3) has resulted in the ability to sequence smaller and smaller sample quantities (mmole to pmol), although the original chemistry has remained essentially unchanged. Current automated instrumentation permits 10–20 cycles of sequence determination on 10–50 pmol of sample.

[1] Cited references are listed in the bibliography.

Advances in protein isolation methodology have recently made it possible to isolate proteins of biological interest which are present in tissues in sub-picomole quantities. Techniques such as 1- and 2-dimensional electrophoresis (with electroblotting to membranes), microcolumn liquid chromatography, and capillary electrophoresis have allowed protein and peptide purification down to the 10–100 femtomole level. Many of these proteins have been shown to have key roles in the development and treatment of human disease. Improved methods of protein sequencing requiring less sample quantity would make it possible to obtain the necessary sequence information in order to clone and express these proteins, thereby making it possible to study the structure function aspects of these important proteins. It is generally anticipated that this information could set the stage for advances in the treatment of human diseases through rationalized drug design and gene therapy.

A major limitation to increasing the sensitivity of protein sequencing down to the femtomolar level involves the intrinsic detectability of the released phenylthiohydantoin (PTH) amino acids. The PTH amino acids, which are detected by absorption at 269 nm, have relatively low extinction coefficients. Intrinsic background noise associated with absorbance measurements at this wavelength and chemical background from the reagents used in sequencing also contribute to the limit of detection. Although a recently published method involving the use of absorbance detection with capillary electrophoresis rather than HPLC for separation of the PTH amino acids has shown femtomolar detection (4), this technique requires subnanoliter injection volumes. Current automated sequencer technologies dissolve the PTH amino acids in a 50–200 $\mu$l volume for injection. The required use of only a small fraction of this volume, e.g., 0.1 nanoliter sample size, would negate any value in the increased sensitivity of detection using capillary electrophoresis.

Numerous attempts have been made to increase the sensitivity of Edman degradation through the use of radiolabeled, chromophoric, or fluorescent isothiocyanate reagents. 4-(N,N'-dimethylamino)azobenzene-4'-isothiocyanate (DABITC), a highly chromophoric reagent first described by Chang et al. (5), has primarily been used as a manual sequencing reagent with a DABITC/PITC double coupling procedure (6), although it has been used in automated solid-phase sequencing (7). More recently, Aebersold et al. (8,9) reported a DABITC solid-phase sequencing method in which proteins were immobilized on DITC-derivatized aminopropyl glass-fiber sheets.

Sequence analysis was performed at the 20–50 picomole level, a substantial improvement over previous methods, but still less sensitive than current gas-phase sequence analysis. Fluorescent reagents, such as fluorescein isothiocyanate (10,11) and dansyl-containing isothiocyanates (12–16) have also been evaluated as sensitivity enhancing reagents. Although synthetic amino acid derivatives prepared using these reagents show subpicomole sensitivity by HPLC analysis, they have not surpassed the sensitivity of gas-phase Edman degradation during automated sequence analysis. In general, it has been found that the use of large bulky chromophores on the isothiocyanate reagent interferes with the efficiency of the derivatization and cleavage reactions of the Edman degradation. The inhibition of the coupling and cleavage reactions with these reagents is postulated to be caused by a combination of steric and electronic effects. The use of radiolabeled reagents has also proven to not be successful, since radiolabeled reagents undergo autoradiodegradation which results in decreasing product yields and increasing amounts of labeled by-products. Modified phenyl isothiocyanates such as 4-(Boc-aminomethyl)-PITC, which are designed to react with post-column fluorescent reagents, have also been investigated (17) but have been found to undergo side reactions during the cleavage reaction resulting in loss of the amino group (14).

An alternative to the use of modified Edman reagents is the reaction of the anilinothiazolinone (ATZ)-amino acid intermediate with sensitivity-enhancing nucleophilic reagents. The use of radiolabeled amines produced amino acid derivatives which could be detected at the femtomole level (18,19), but the handling of radioactive materials was inconvenient. Horn et al. (20) have extended earlier studies on the use of MeOH/HCl as a conversion reagent (21) to include chromophoric or fluorophoric alcohols, resulting in the formation of phenylthiocarbamyl amino acid esters. Tsugita et al. (22) have recently reported a modification of the Edman degradation scheme, in which ATZ amino acids are reacted with 4-aminofluorescein resulting in highly fluorescent, phenylthiocarbamyl amino acid aminofluorescein amides (PTCAF-amino acids) (FIG. 2). PTCAF-amino acids were separated by reversed-phase HPLC and were detectable at the 0.1–1 femtomole level. Several known and unknown protein samples were reported to be sequenced at the 100 femtomole to 10 picomole level using an Applied Biosystems 477A sequencer. Poor yields are obtained when certain amino acids are encountered, e.g., Glu, Ser, Thr, His. No yields at all are obtained when sequencing through Asp.

Although this approach can work, it suffers from a number of problems which make it of little practical value toward the goal of more sensitive sequencing. The most serious difficulty with this method, in its present form, is the low yields obtained with the hydrophilic amino acids, in particular threonine, histidine, glutamate, lysine, and glutamine, and the total lack of yield obtained with aspartate. These low yields were found to result from the uncontrolled rearrangement of the thiazolinone produced during the Edman reaction to the unreactive thiohydantoin derivative (33). Recent studies concerning the aminolysis of the ATZ-amino acids by Pavlik et al. (23) showed that many of the ATZ-amino acids, in particular the hydrophilic amino acids, can rearrange so rapidly to the more thermodynamically stable PTH amino acids that by the time the ATZ-amino acid is brought over to the conversion flask of an automated instrument, anywhere from 5–70% of the amino acid has already been converted. Once an ATZ-amino acid has converted to a PTH, it would not be capable of reacting with aminofluorescein. This explanation is consistent with applicant's observed data. By analogy with the data presented above, it is anticipated that any chemical scheme that relies on tagging the ATZ analogue with a fluorescent molecule, such as reaction of the ATZ analogues with alcohols (20), will not offer any practical gains in the sensitivity of N-terminal microsequencing.

An Edman type reagent which produced positively charged amino acid analogues optimal for detection by electrospray mass spectrometry has been described by Aebersold, et al. (34, 35). This chemistry requires covalent coupling of the sample to be sequenced.

The present status of microsequence analysis, protein and peptide purification, and other related techniques was the subject of a recent review (24) and a number of recent monographs (25–30). It was concluded that improvement in analytical techniques such as microsequence analysis was necessary in order to match the capability of known purification methods. Improvements in microsequence analysis could have far reaching effects. For example, the ability to detect differences in complex biological samples such as cerebrospinal fluid by 2D-electrophoresis (31) and also obtain meaningful sequence information could be of great importance in understanding various pathological states.

SUMMARY OF THE INVENTION

This invention entails a novel utilization of certain thiocarbonyl compounds and alcohols to synthesize a reagent useful for N-terminal polypeptide sequencing. The N-terminal amino acid is derivatized with the reagent to produce an alkoxy thiourea derivative at the N-terminus of the polypeptide to be sequenced. The derivatized polypeptide is then treated with acid to specifically remove the N-terminal amino acid as a thiazolinone derivative which cannot rearrange to a thiohydantoin. This thiazolinone derivative can be further reacted with another molecule to form a derivative optimally detectable by any one of a multitude of techniques including electrospray mass spectrometry. Such alternative detection techniques provide a means of improving sequencing sensitivity from the current picomolar range to the femtomolar range. The methods of the invention are readily automated using presently available instrumentation.

DESCRIPTION OF THE FIGURES

FIG. 7 also depicts the reversed phase HPLC analysis of the fluorescent products formed during the reaction of MTZ aspartate with dansyl ethylenediamine (Example V).

DETAILED DESCRIPTION OF THE INVENTION

The vast majority of reagents that have been utilized to place a fluorescent or highly chromophoric tag on the released thiohydantoin amino acid have relied on the isothiocyanate group as the electrophilic group used to mediate the coupling reaction. Isothiocyanates form a thiourea group with the N-terminal amino acid. The sulfur atom of the thiourea is thus perfectly placed so that upon acidification a kinetically favored five-numbered thiazolinone ring could form which specifically cleaves only the N-terminal amino acid. Most chromophoric and fluorescent compounds are relatively large when compared to the phenyl ring of phenyl isothiocyanate (PITC, the reagent commonly used for N-terminal protein sequencing). Typically, when a large chromophoric compound that contains a reactive isothiocyanate group is substituted for PITC, the coupling and/or cleavage reaction is kinetically disfavored by a combination of steric and electronic effects. This results in poor initial and repetitive yields of sequencing.

Figure 1:
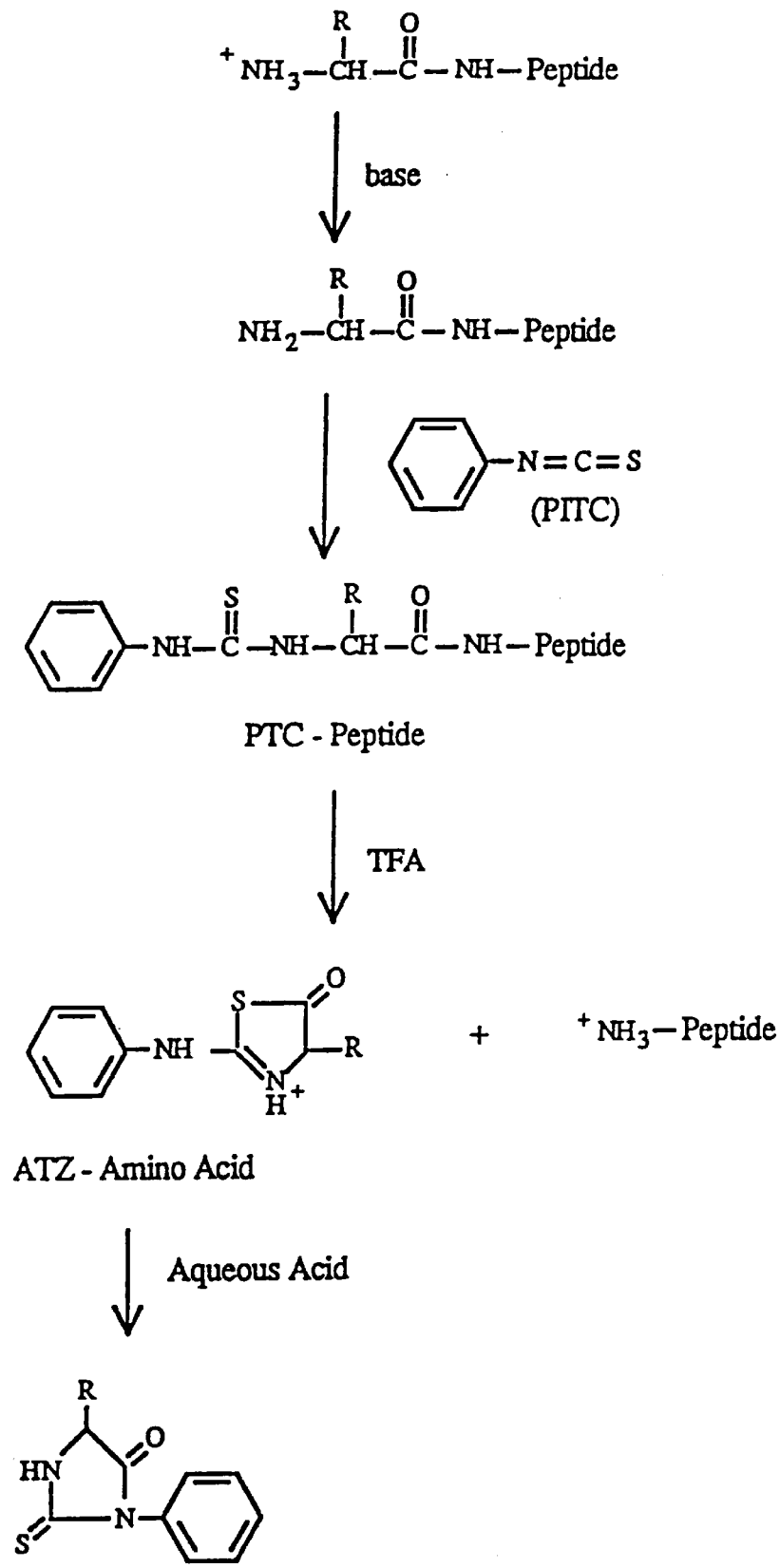
FIG. 1 (prior art) depicts Edman chemistry for N-terminal protein sequencing.
Figure 2:
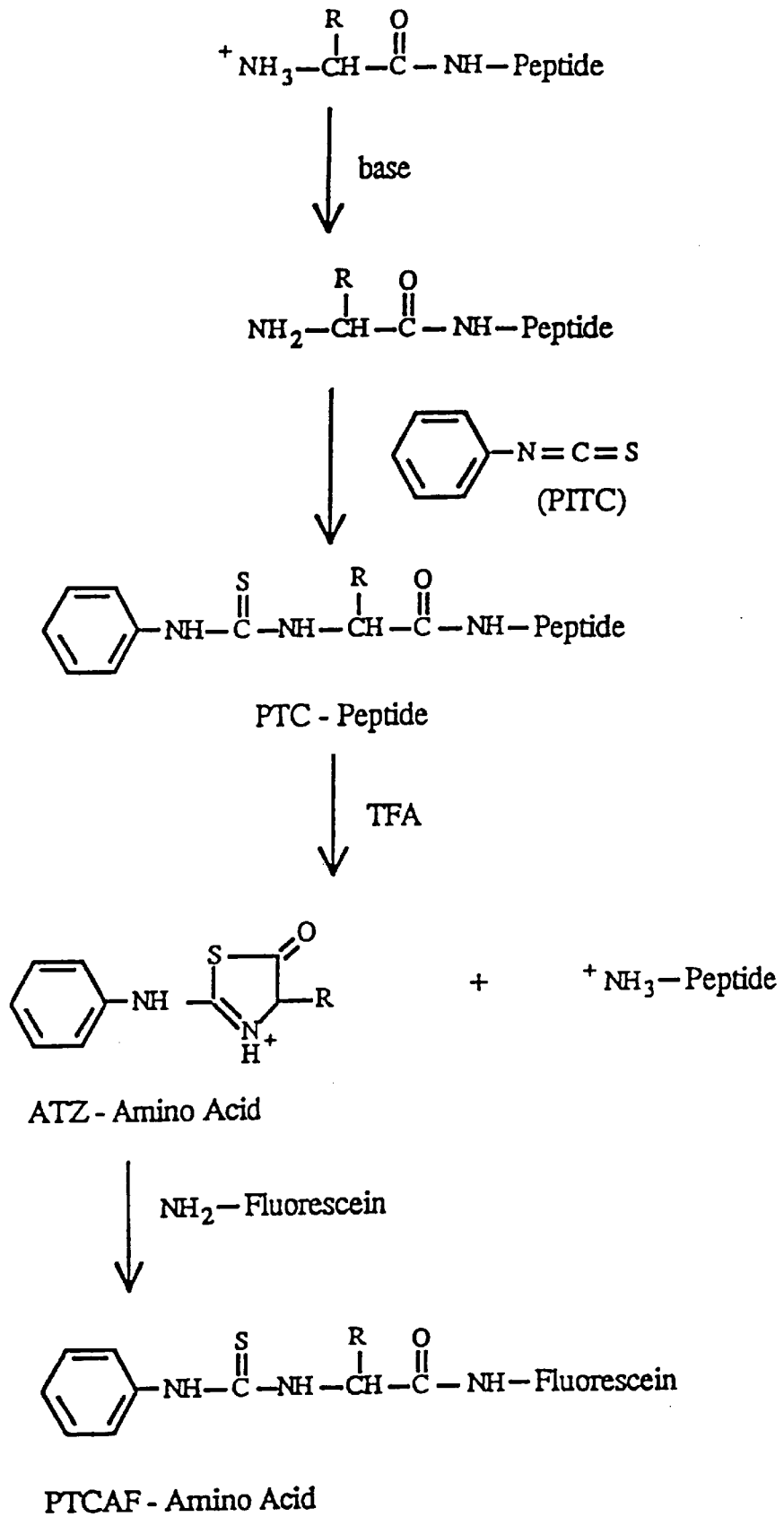
FIG. 2 (prior art) depicts a modification of the Edman chemistry described by Tsugita, et al. (19).

An alternative procedure for introducing a fluorescent or chromophoric tag onto the released amino acid has relied upon reaction of the anilinothiazolinone (ATZ) analogue (FIG. 1), formed during the normal Edman degradation, with a nucleophilic amine (22) or fluorescent alcohol (20). Both of these techniques assume that the thiazolinone analogue formed during sequencing is stable long enough for the nucleophilic chromophore to be added. However, in actual practice, this assumption has turned out not to be entirely true. A recent study (23) has shown that in fact a significant portion of the ATZ amino acids immediately rearrange to their more thermodynamically stable thiohydantoin analogues. Once the thiohydantoin analogue has formed, it can no longer be reacted with a nucleophilic tag to form the desired fluorescent derivative. This rearrangement to the more thermodynamically stable thiohydantoin was observed to be more pronounced with the more hydrophilic amino acids. This observation is consistent with the data observed from applicant's laboratory when automated sequencing was performed with the aminofluorescein procedure described by Tsugita et al. (22). The yields of sequencing obtained with the hydrophilic amino acids were poor and nonexistent for aspartic acid. By contrast, the yields obtained with the hydrophobic amino acids were observed to be good. In general, it can be concluded that reaction of the thiazolinone derivative obtained during normal Edman chemistry with a nucleophilic amine or hydroxyl molecule containing a fluorescent or chromophoric tag will not be a practical method for increasing the sensitivity of N-terminal sequence analysis (to require less sample for analysis) since the thiazolinone derivative of the hydrophilic amino acids, especially aspartate, rearranges too rapidly to the unreactive thiohydantoin derivative and therefore prevents efficient tagging of these amino acids. One method to solve this problem is to produce during sequencing a thiazolinone derivative which cannot rearrange to a thiohydantoin derivative and thus would be capable of quantitative derivatization with an amine or hydroxyl nucleophile containing a chromophoric or fluorescent group. The formation of such a stable thiazolinone and subsequent tagging with a group optimal for various methods of detection is the subject of this invention.

Accordingly, an important aspect of this invention entails sequencing reagents useful to form an alkoxythiourea derivative at the N-terminus of a polypeptide to be sequenced. Such reagents have the formula I:

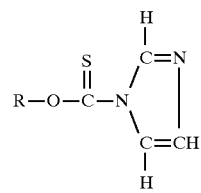

in which R is a straight or branched chain alkyl group having 1 to 8 carbon atoms or a phenyl group. Alkyl groups designated by R include, but are not limited to, methyl, ethyl, propyl, isopropyl, pentyl, isopentyl, hexyl, isohexyl, heptyl, isoheptyl, octyl and isoactyl groups. Preferable R is a methyl group such that the Formula I reagent is methoxythiocarbonylimidazole (MTCI).

Formula I compounds may be synthesized by reaction of an alkanol having 1 to 8 carbon atoms or phenol with a thiocarbonyldiimidazole. For example, MTCI may be synthesized by reaction of methanol with thiocarbonyldiimidazole. The reaction is preferably accomplished at a temperature of 2520 C. to 70° C. by addition of the alkanol or phenol to a solution containing alcohol and thiocarbonyldiimidazole in a ratio of 1.5:1.0 respectively in dimethylformamide or acetonitrile.

Figure 3:
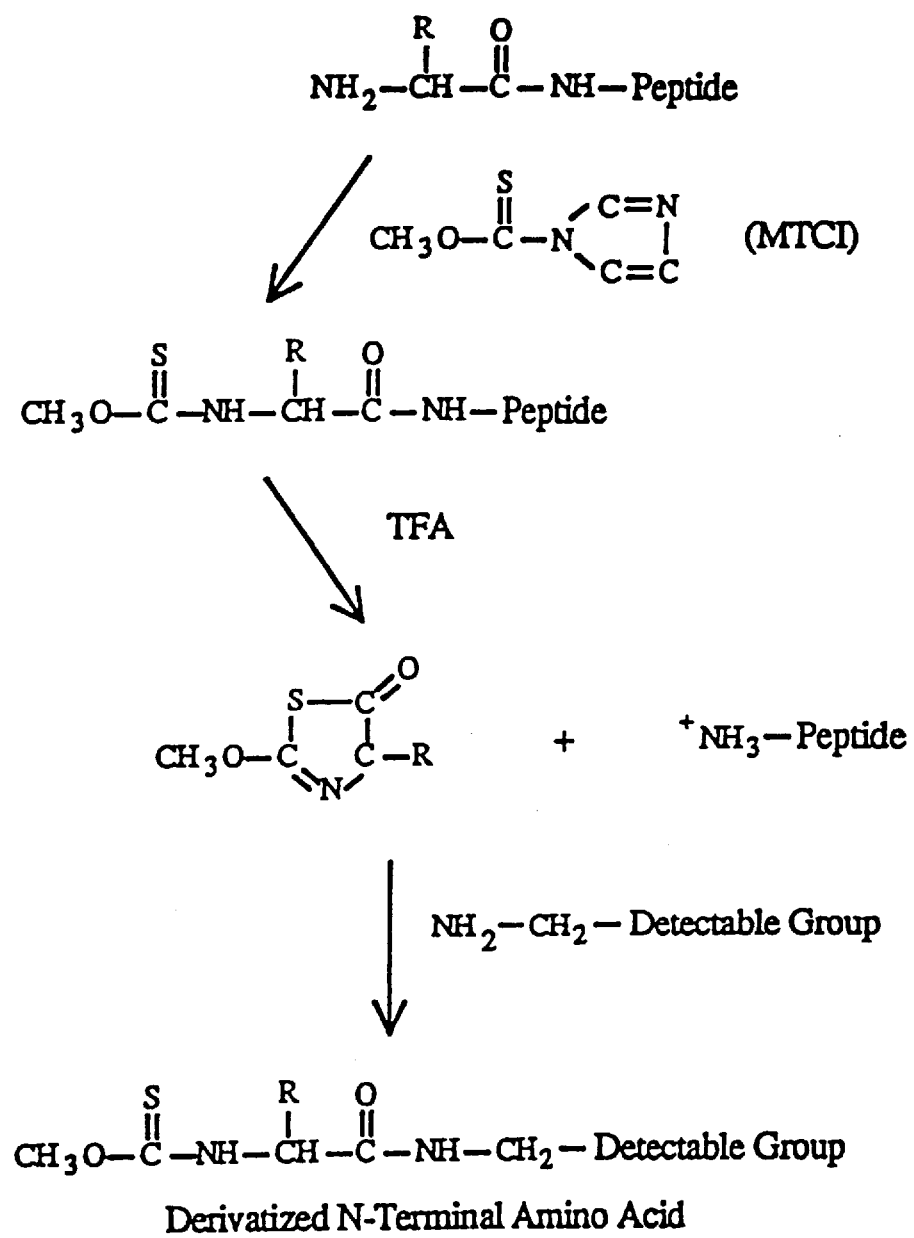
FIG. 3 depicts one embodiment of the N-terminal protein sequencing chemistry provided by this invention.

The chemistry which can form a stable thiazolinone is shown in FIG. 3. The Formula I reagent, such as methoxythiocarbonylimidazole (MTCI), used for derivatization is first synthesized by reaction with methanol and thiocarbonyldiimidazole. The imidazoles so formed, such as MTCl, are stable in solvents such as acetonitrile for at least one week at room temperature. These reagents are then used for reaction with the N-terminus of the polypeptide to be sequenced. The derivatized peptide is cleaved in known manner, e.g., with trifluoroacetic acid (TFA), hexafluorobutyric acid or hydrochloric acid to form a thiazolinone derivative. The thiazolinone derivative so formed is then treated with an amino containing nucleophile which contains a group optimal for detection, for example, a fluorophore for fluorescent detection, or a highly chromophoric reagent for ultraviolet or visible absorbance detection, or an amino nucleophile containing an easily ionized or permanently ionized group for mass spectral detection.

In the preferred practice of the invention, a solution containing 100 picomoles to 0.5 micromoles polypeptide to be sequenced is reacted at 25° C. to 70° C. with a solution containing 0.5 micromoles to 100 millimoles of the selected Formula I reagent. Three appropriate solvents are dimethyl formamide, acetonitrile and methanol.

The method may be conducted through any desired or necessary number of cycles. There is no limitation on the size of the polypeptide that may be sequenced. In many instances, however, the polypeptide will contain 2 to 500 amino acid residues.

The protein or peptide to be sequenced can be attached either covalently or non-covalently to various solid supports currently used in the field. Examples include PVDF, glass fiber filters, silica beads, polyethylene, carboxyl modified polyethylene or PVDF, and porous polytetrafluoroethylene (Zitex). The peptide or protein is then derivatized with the reagent indicated in FIG. 3 to form a peptidyl derivative. The cleavage reaction is then performed with liquid or gaseous trifluoroacetic acid or other acid such as hydrochloric acid to form the thiazolinone amino acid. Trifluoroacetic acid (TFA) is preferred. The thiazolinone so formed is then treated with a fluorescent amine or other suitable reagent. Examples of suitable fluorescent amines which have been found to react with thiazolinones formed with this chemistry include dansyl cadaverine and aminomethylfluorescein.

Pursuant to this invention, the thiazolinone formed is derivatized with any one of a number of groups which could then be utilized to permit many different types of detection in addition to fluorescence or ultraviolet. Such examples include mass spectrometry, chemiluminescence, and electron capture.

EXAMPLE I

Synthesis of Methoxythiocarbonylimidazole (MTCI) by Reaction of Methanol and Thiocarbonyldiimidazole Methanol (7.6 mmol) was added to 1,1'-thiocarbonyldiimidazole (5 mmol in 15 ml acetonitrile). The reaction was stirred at 50° C. for 1 hour. The presence and structure of MTCI was confirmed by FAB mass spectrometry. The expected MH+=143 was obtained.

Reagent compounds useful in the invention may be synthesized in like manner by the reaction of 2 to 8 carbon atom straight or branched chain alkanols (ROH in which R is a 2 to 8 carbon atom alkyl group) with thiocarbonyldiimidazole.

The invention also includes the use of the reaction products of 1 to 8 carbon atom alkanols with thiocarbonyl compounds that provide different leaving groups. Such thiocarbonyls include:

1,1'-thiocarbonyldi-(1H)-pyridone:

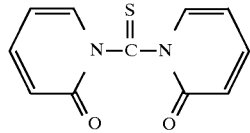

which reacts with ROH to provide alkoxy(2-hydroxypyridyl) thiocarbonyl,

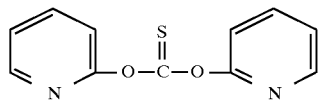

which reacts with ROH to provide alkoxy(2-pyridylthionocarbonate), and bis(carboxymethyl) trithiocarbonate

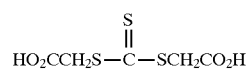

which reacts with ROH to provide alkoxy(2-thiocarboxymethyl)thiocarbonyl.

EXAMPLE II

Reaction of the Tripeptide DYM with MTCI

Figure 4:
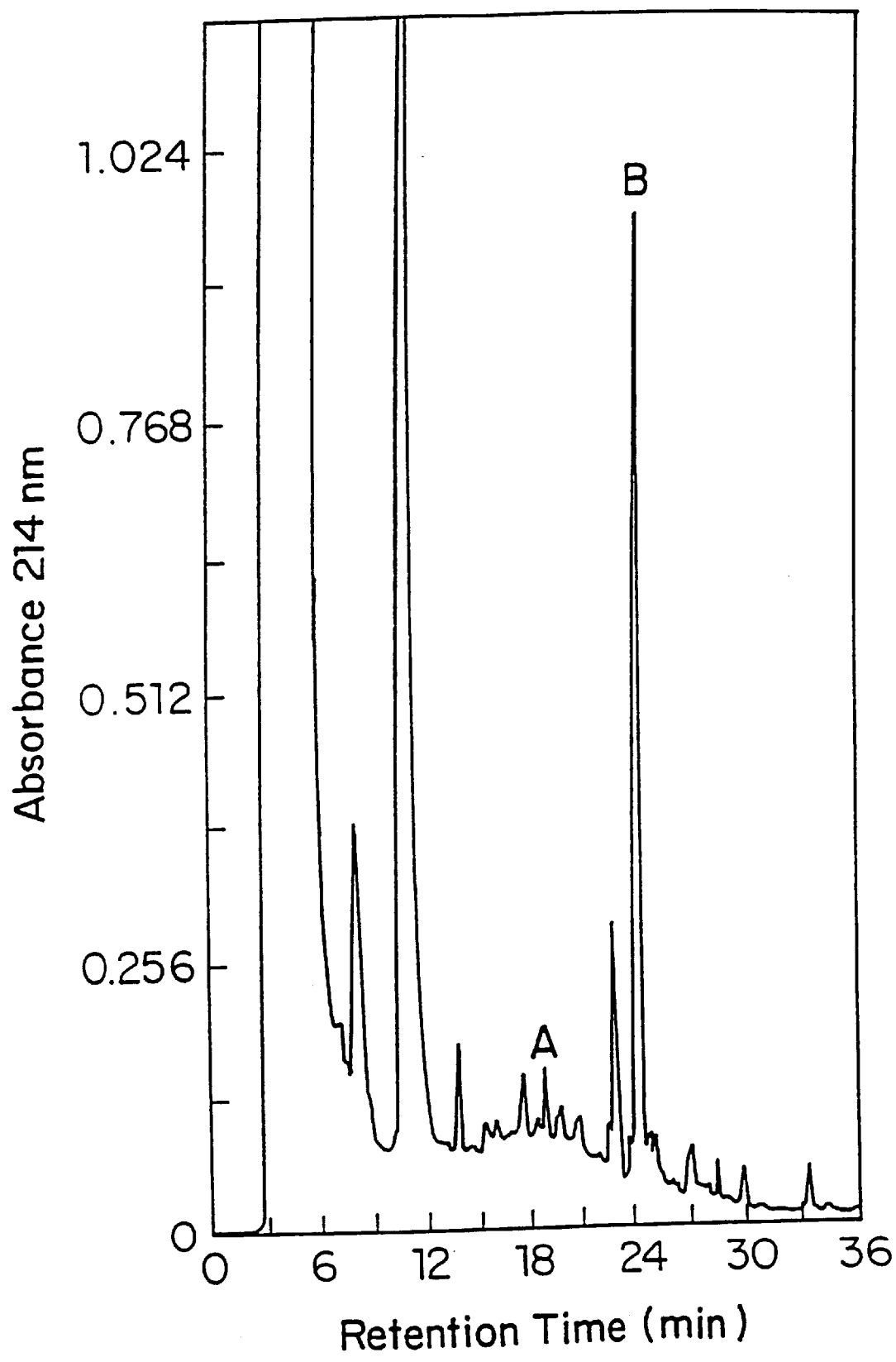
FIG. 4 depicts the reversed phase HPLC analysis of sample described in Example II. Peak A is the starting peptide DYM. Peak B is the expected N-terminal methoxythiocarbonyl derivative.
Figure 5:
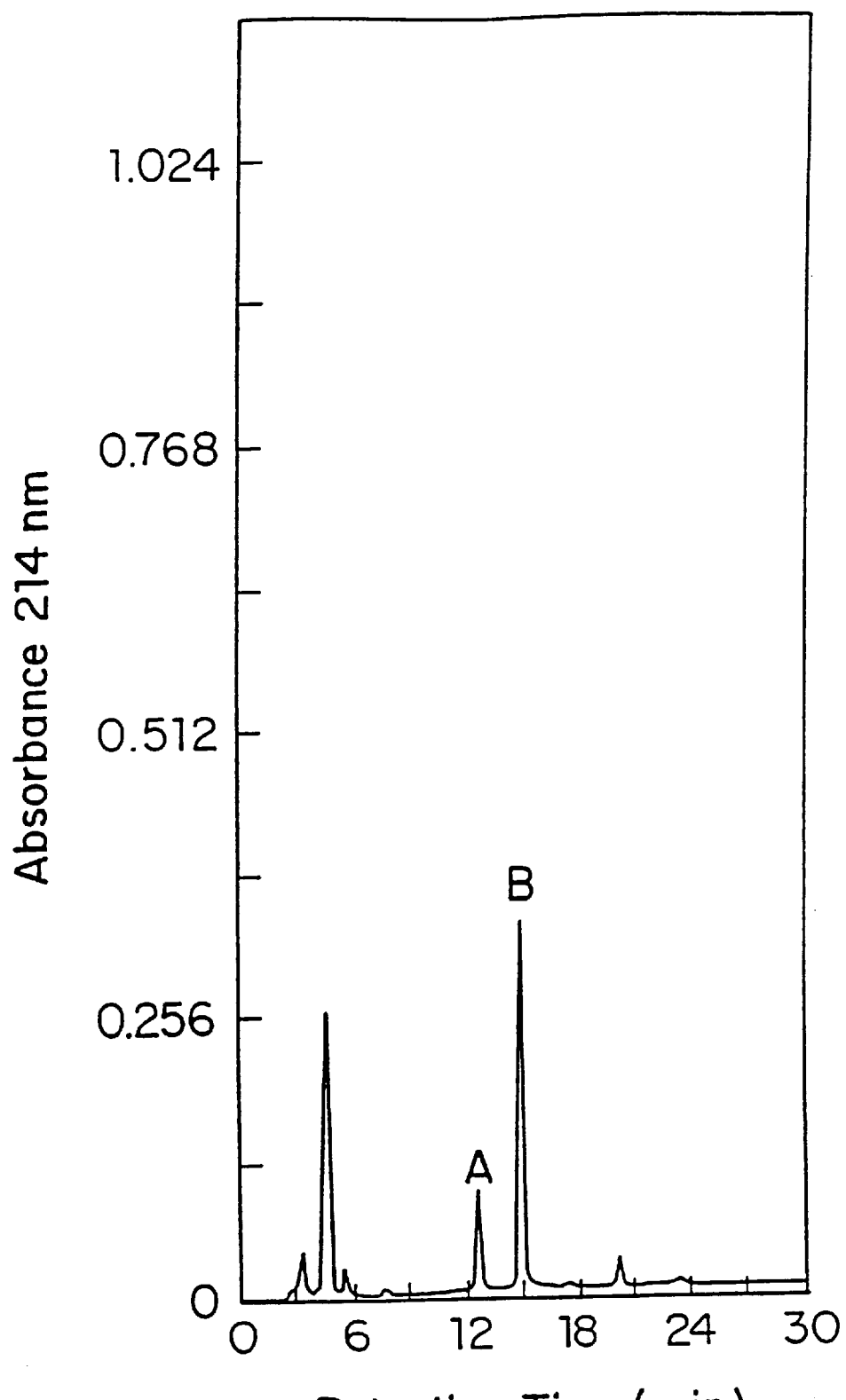
FIG. 5 depicts the reversed phase HPLC analysis of Peak B after reaction with trifluoroacetic acid. Peak A is the methoxythiocarbonyl amino acid. Peak B is the shortened peptide.

MTCI (10 µl) in 100 µl of acetonitrile was added to the tripeptide, DYM (100 nmole) in 100 µl of dimethylformamide (DMF). The reaction was incubated at 50° C. for 30 minutes. The sample was then taken to dryness in a vacuum centrifuge, redissolved in 0.1% trifluoroacetic acid in water (100 µl), and analyzed by reversed phase HPLC (FIG. 4). The expected peptide product (the N-terminal methoxythiocarbonyl derivative; peak B) was identified by FAB/MS (MH+=502) and obtained in approximately 95% yield. Peak A is the starting peptide, DYM (MH+=428). Peak B was then treated with 100 µl of anhydrous trifluoroacetic acid (TFA) for 15 minutes at 5020 C., dried in a vacuum centrifuge, redissolved in 0.1% trifluoroacetic acid in water (100 µl), and analyzed by reversed phase HPLC (FIG. 5). The shortened peptide (DYM, Peak B) (MH+=313) and the methoxythiocarbonyl amino acid (Peak A, MH+=208) were found in quantitative yield.

EXAMPLE III

Figure 6:
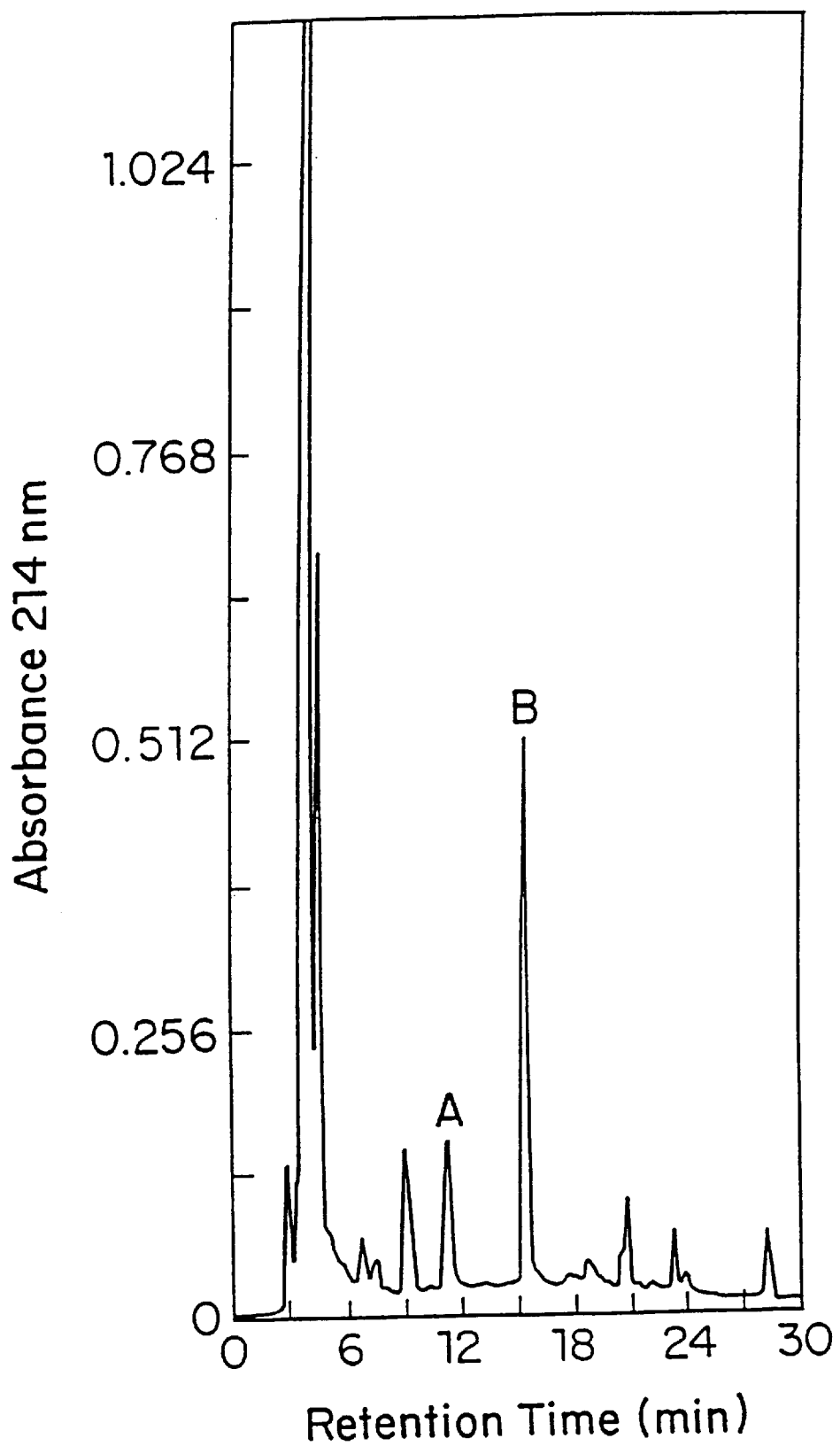
FIG. 6 depicts the reversed phase HPLC analysis of the sequencing reaction described in Example III.

Reaction of Methoxythiocarbonyl Thiazolinone Aspartate With Dimethylaminopropylamine In a separate experiment, the dried TFA cleavage reaction of the DYM peptide was dissolved in 100 µl DMF containing 5 µl of dimethylaminopropylamine and incubated for 30 minutes at 50° C. The reaction was taken to dryness, redissolved in 0.1% trifluoroacetic acid in water (100 µl), and analyzed by reversed phase HPLC (FIG. 6). The shortened peptide (YM) (Peak B, MH+=313) and the methoxythiocarbonyl aspartate (dimethylaminopropyl)amide (Peak A, MH+=292) were found in quantitative yield. The dimethylaminopropylamino group has been previously found to be useful for detection by mass spectrometry (32).

EXAMPLE IV

Figure 7:
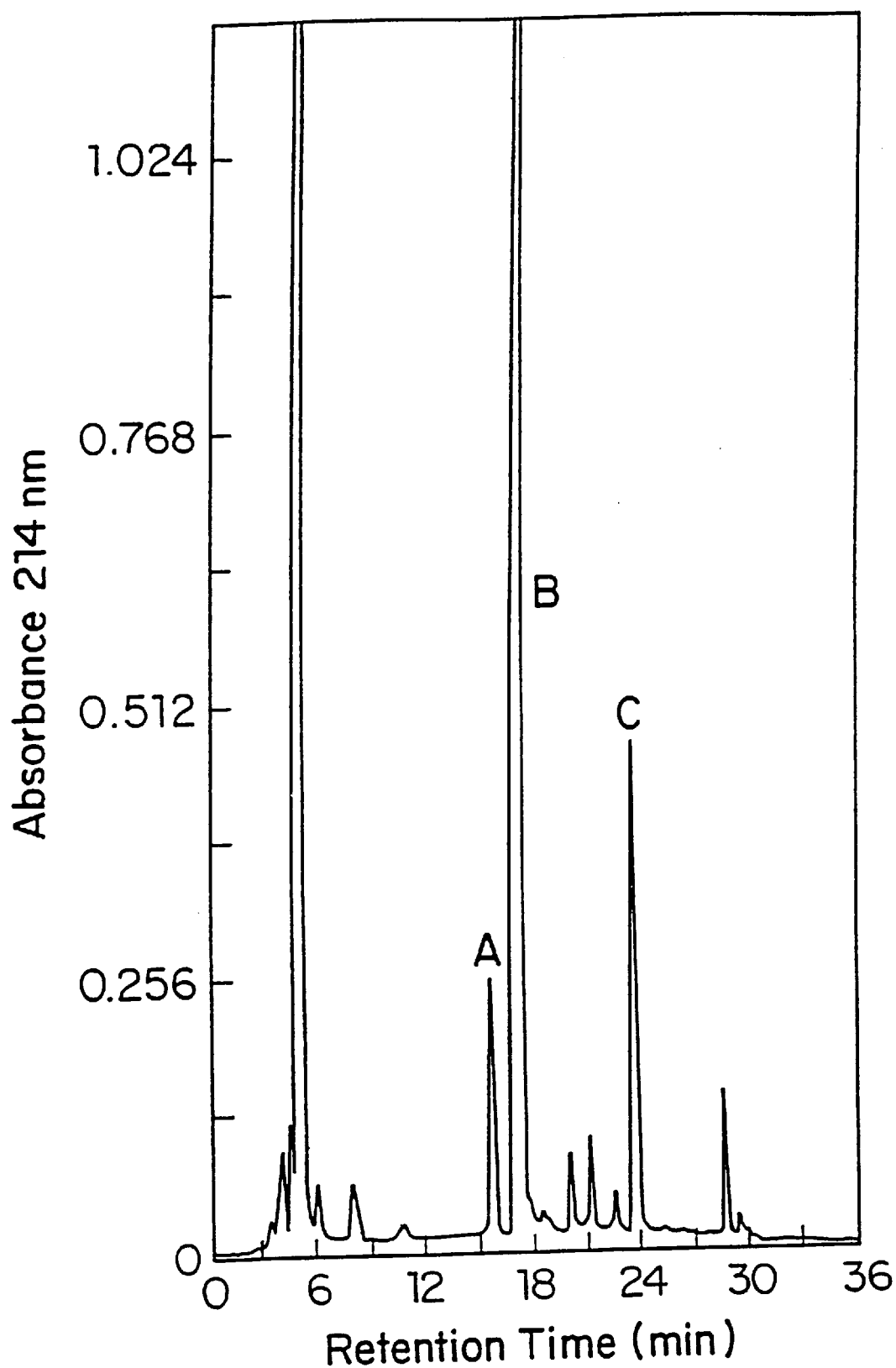
FIG. 7 depicts the reversed phase HPLC analysis of the sequencing reaction described in Example IV.

Reaction of Methoxythiocarbonyl Thiazolinone Aspartate With Dansyl Ethylenediamine In a separate experiment, the dried TFA cleavage reaction of the DYM peptide was dissolved in 100 µl DMF containing 5 µnmole of dansyl ethylenediamine and incubated for 15 minutes at 50° C. The reaction was taken to dryness, redissolved in 0.1% trifluoroacetic acid in water (100 µl), and analyzed by reversed phase HPLC (FIG. 7). The shortened peptide (YM) Peak C, MH+=313) and the methoxythiocarbonyl aspartate (dansyl ethyleneamine)amide (Peak A, MH+=483) were found in quantitative yield. Peak B is excess dansyl ethylenediamine. The dansyl ethyleneamino group is suitable for detection of the amino acid analogues by fluorescence.

EXAMPLE V

HPLC Analysis of the Products Formed During the Reaction of MTZ-Aspartate With Dansyl Ethylenediamine The dried TFA cleavage reaction of the DYM peptide was dissolved in 100 µl DMF containing 5 µnmole of dansyl ethylenediamine and incubated for 15 minutes at 50° C. The reaction was taken to dryness, redissolved in 0.1% trifluoroacetic acid in water (100 µl), and analyzed by reversed phase HPLC. Referring to FIG. 7 the shortened peptide (YM) (Peak C, MH+=313) and the methoxythiocarbonyl aspartate (dansyl ethyleneamine)amide (Peak A, MH+=483) were found in quantitative yield. Peak B is excess dansyl ethylenediamine.

Peptides which have been successfully derivatized with MTCI and subsequently cleaved with TFA in like manner include: DYM, LAP, TVL, GW, AFP, YGLDVF, and YGGFL.

DETECTION OF THE RELEASED AMINO ACID BY MASS SPECTROMETRY

Recent advances have made the use of a mass spectrometer as a means of detection of the released amino acid, in place of chromatographic methods, a viable option. The potential advantages include: speed, sensitivity, and the ability to analyze post-translationally modified amino acids since detection is based on mass and not retention time. In order to be successful, an easily ionized functional group must be placed on the amino acid to be detected. A number of isothiocyanate based reagents have been described for this purpose. These include: 4-nitrophenylisothiocyanate (36), 3-[4'(ethylene-N,N,N-trimethylamino)phenyl]-2-isothiocyanate (34), and dimethylaminopropylisothiocyanate (32). An alternative method based on the thiobenzoylation chemistry has also been proposed (37). Previous work with the dimethylaminopropylisothiocyanate showed that thiohydantoin amino acids could be easily synthesized with a dimethylaminopropyl group and that they could be detected at the 20–50 femtomole level by electrospray mass spectrometry. However, initial experiments aimed at the automation of this chemistry showed that solvents capable of extraction of the positively charged amino acid analogues formed by the TFA cleavage reaction also caused washout of the sample to be sequenced. One solution to this problem is to covalently attach the sample to be sequenced to a solid support.

Figure 8:
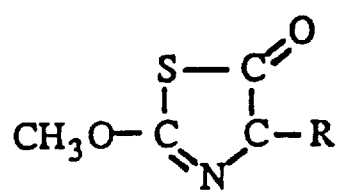
FIG. 8 depicts the reaction of a methoxythiazolinone (MTZ) amino acid derivative with dimethylaminopropylamine to produce an amino acid derivative detectable by mass spectrometry.
Figure 8:
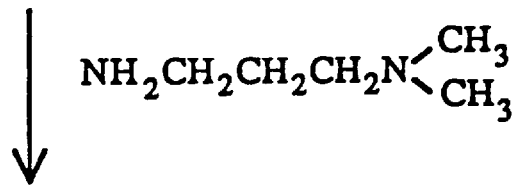
Figure 8:
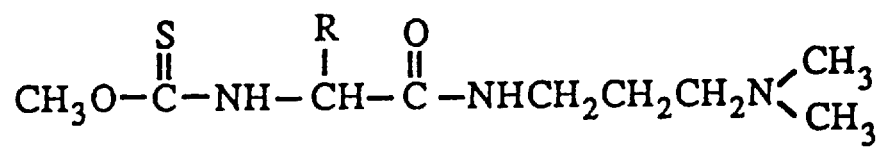

This invention provides a more attractive solution in which the positively charged group needed for mass spectrometry is not introduced until after the extraction reaction. The thiazolinone formed in FIG. 3 is extracted to the conversion flask of the automated sequencer and then reacted with dimethylaminopropylamine prior to introduction into the mass spectrometer as shown by FIG. 8.

This chemistry has a number of advantages over other previously described chemistries for mass spectrometric detection. These include:

1. A laborious reagent synthesis is not required.
2. The addition of the charged functional group after formation of the amino acid analogue permits the use of a wide variety of charged groups and permits a wider range of mass separation between reagent by-products and the amino acid analogues. Charged groups optimal in terms of mass and ionization can be chosen.
3. The non-covalent application of sample permits routine automated sequence analysis.

EXAMPLE VI

Kinetics of Reaction of YGGFL with MTCI

Figure 9A:
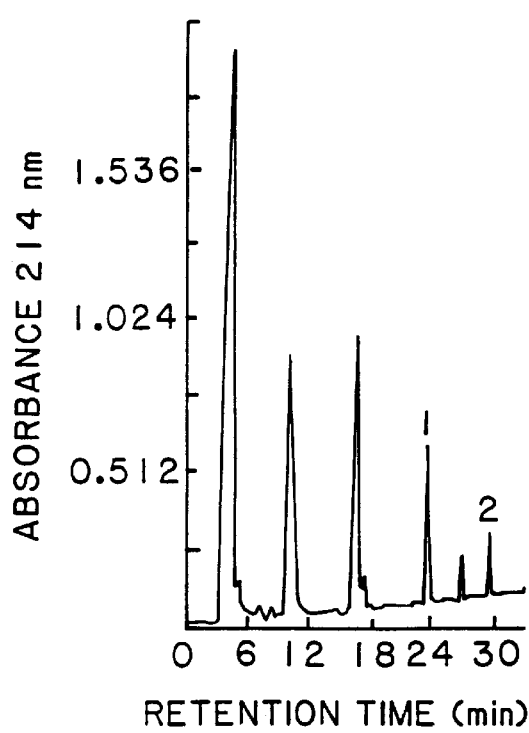
FIG. 9 depicts reverse phase HPLC analysis of the reaction of YGGFL with MTCI (Example VI).
Figure 9B:
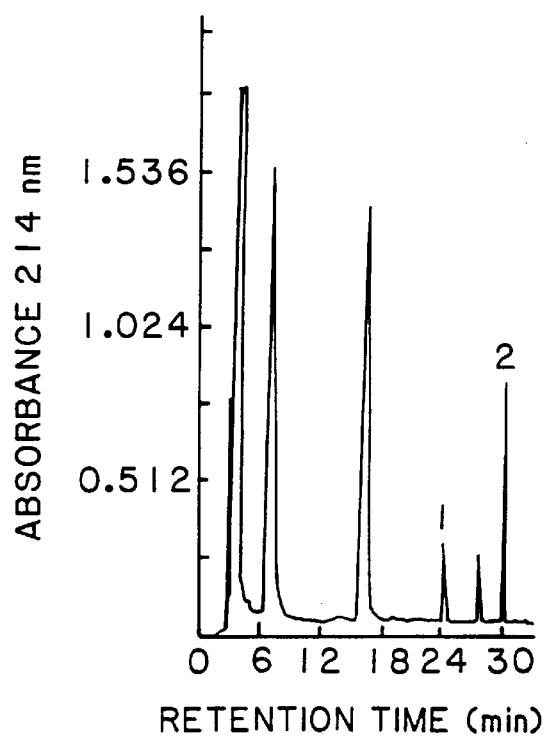
Figure 9C:
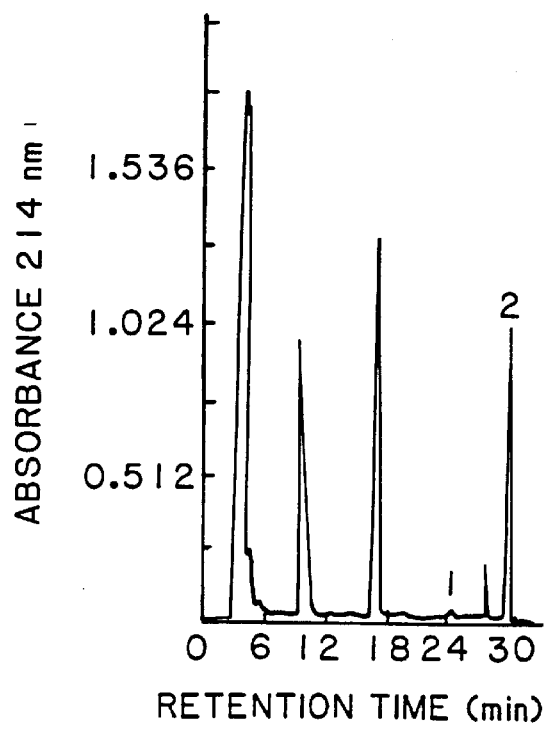

MTCI (1.3 μnmole) in 2.5 μl of acetonitrile was added to the pentapeptide, YGGFL (35 μnmole in 10 μl of methanol. The reaction was incubated at 50° C. At the indicated times aliquots were withdrawn and analyzed by reverse phase HPLC (FIG. 9). The expected peptide product (the N-terminal methoxythiocarbamyl derivative; peak 2) was identified by FAB/MS (MH+=630). Peak 1 is the starting peptide, YGGFL (MH+=556). The reaction is complete within 30 minutes at 50° C. under these conditions. Higher MTCI to peptide ratios result in faster reaction rates.

EXAMPLE VII

Figure 10:
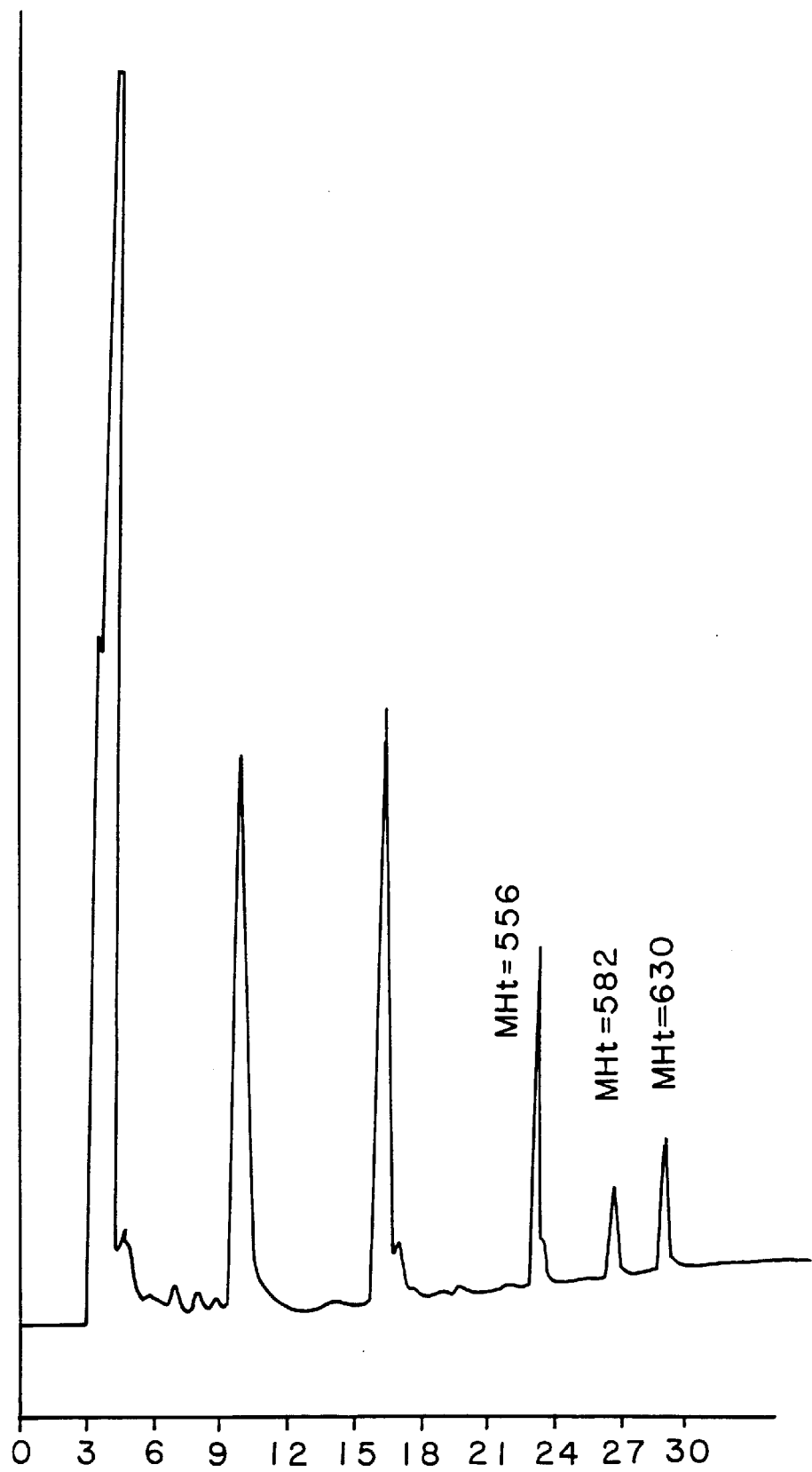
FIG. 10 depicts reverse phase HPLC of the reaction of the methoxythiocarbonyl derivative of YGGFL with trifluoroacetic acid (Example VII).

Reaction of the Methoxythiocarbamyl Derivative of YGGFL With Trifluoroacetic Acid The MTC derivative of YGGFL (peak 2, FIG. 9) was treated with 400 μl of anhydrous trifluoroacetic acid (TFA) at 50° C. Aliquots (50 μl) were withdrawn at the indicated times and 200 μl of water added to quench the reaction. The samples were dried in a vacuum centrifuge, redissolved in 0.1% trifluoroacetic acid in water (100 μl), and analyzed by reversed phase HPLC (FIG. 10). The shortened peptide (GGFL, Peak 1) (MH+=393) and the methoxythiocarbamyl amino acid co-eluted under the conditions used for chromatography. Peak 2 is the uncleaved MTC-YGGFL (MH+=630). The reaction was found to be complete within ten minutes.

EXAMPLE VIII

Figure 11:
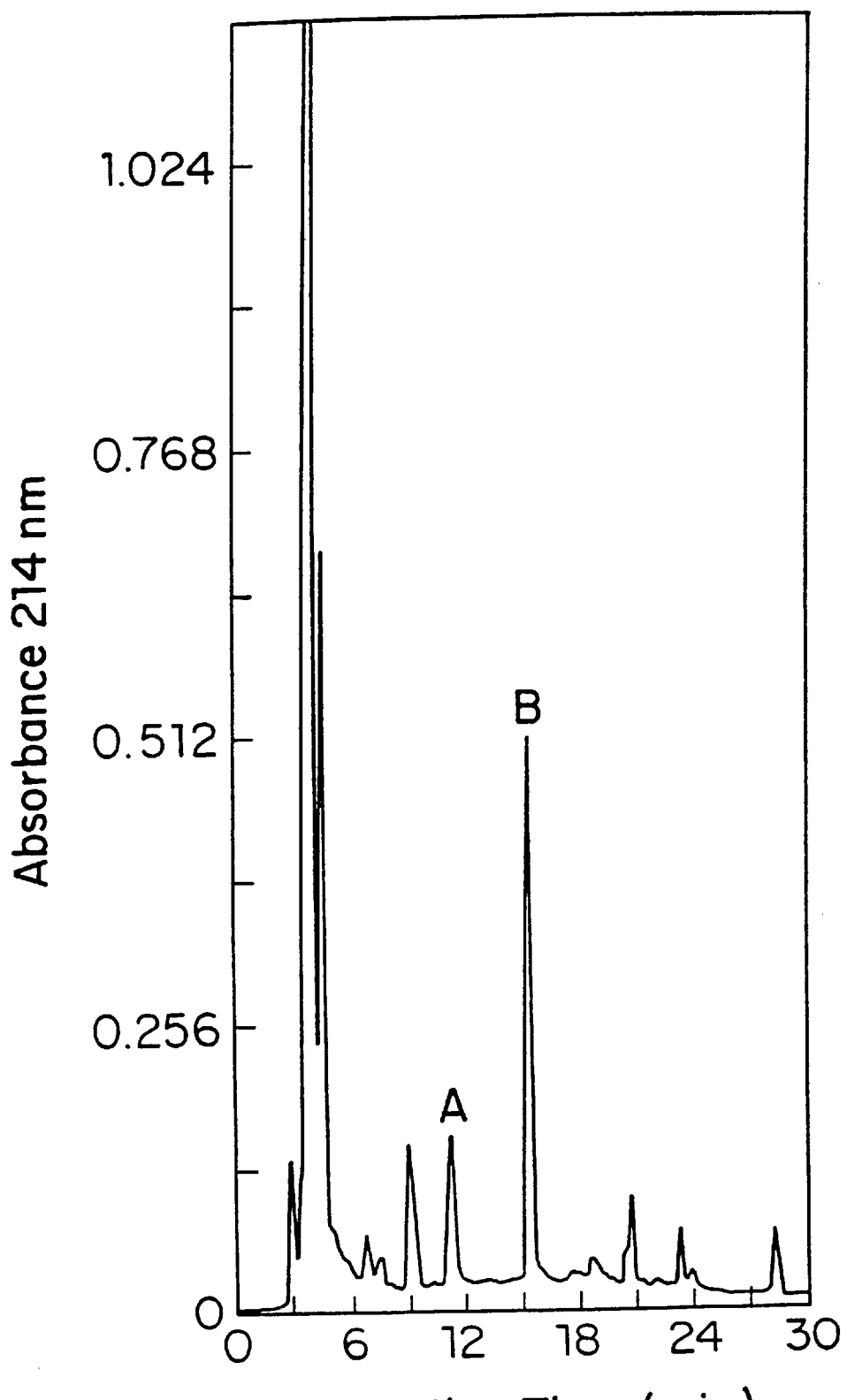
FIG. 11 depicts the reverse phase HPLC analysis of products formed during the reaction of MTZ aspartate with dimethylaminopropylamine (Example VIII).

HPLC Analysis of the Products Formed During the Reaction of MTZ-Aspartate With Dimethylaminopropylamine The dried TFA cleavage reaction of the DYM peptide was dissolved in 100 μl DMF containing 5 μof dimethylaminopropylamine and incubated for 30 minutes at 50° C. The reaction was taken to dryness, redissolved in 0.1% trifluoroacetic acid in water (100 μl), and analyzed by reversed phase HPLC. In FIG. 11 the shortened peptide (YM) (Peak B, MH+=313) and the methoxythiocarbonyl aspartate (dimethylaminopropyl)amide (Peak A, MH+=292) were found in quantitative yield.

Detection of the Released Amino Acid by Fluorescence

The introduction of a fluorescent group to the amino acid derivative formed during sequencing has proven to be problematic. The most commonly employed approach has relied on placing an isothiocyanate functionality onto a highly chromophoric or fluorescent molecule. Since most chromophoric and fluorescent compounds are relatively large when compared to the phenyl ring on PITC, the coupling and/or cleavage reaction is kinetically disfavored by a combination of steric and electronic effects. This problem results in poor initial yields and large lags from cycle to cycle.

An alternative method for introduction of a fluorescent group involved the reaction of the ATZ derivative normally formed during the Edman chemistry with a fluorescent amine (22). This approach suffered from low yields of derivatization of the hydrophilic amino acids (in particular aspartic acid). This was found to result from the uncontrolled conversion to the unreactive thiohydantoin derivative under automated sequencing conditions (33).

Figure 12A:
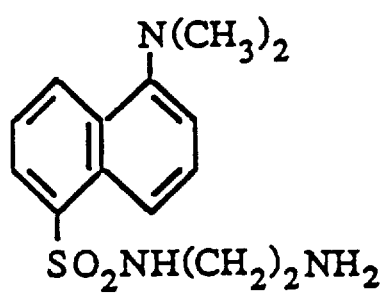
FIG. 12A is the formula of dansyl ethylenediamine.
Figure 12B:
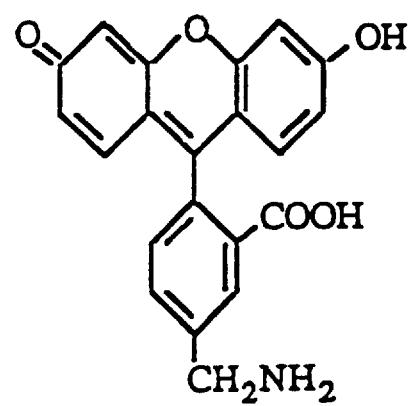
FIG. 12B is the formula of 5-(aminomethyl)fluorescein.

This invention solves this problem using sequencing chemistry which forms a thiazolinone derivative which is incapable of rearranging to a thiohydantoin and which can be quantitatively derivatized with a fluorescent amine reagent (FIG. 3). Dansyl ethylenediamine (FIG. 12A) and 5-(aminomethyl)fluorescein (FIG. 12B) are representative.

EXAMPLE IX

Figure 13:
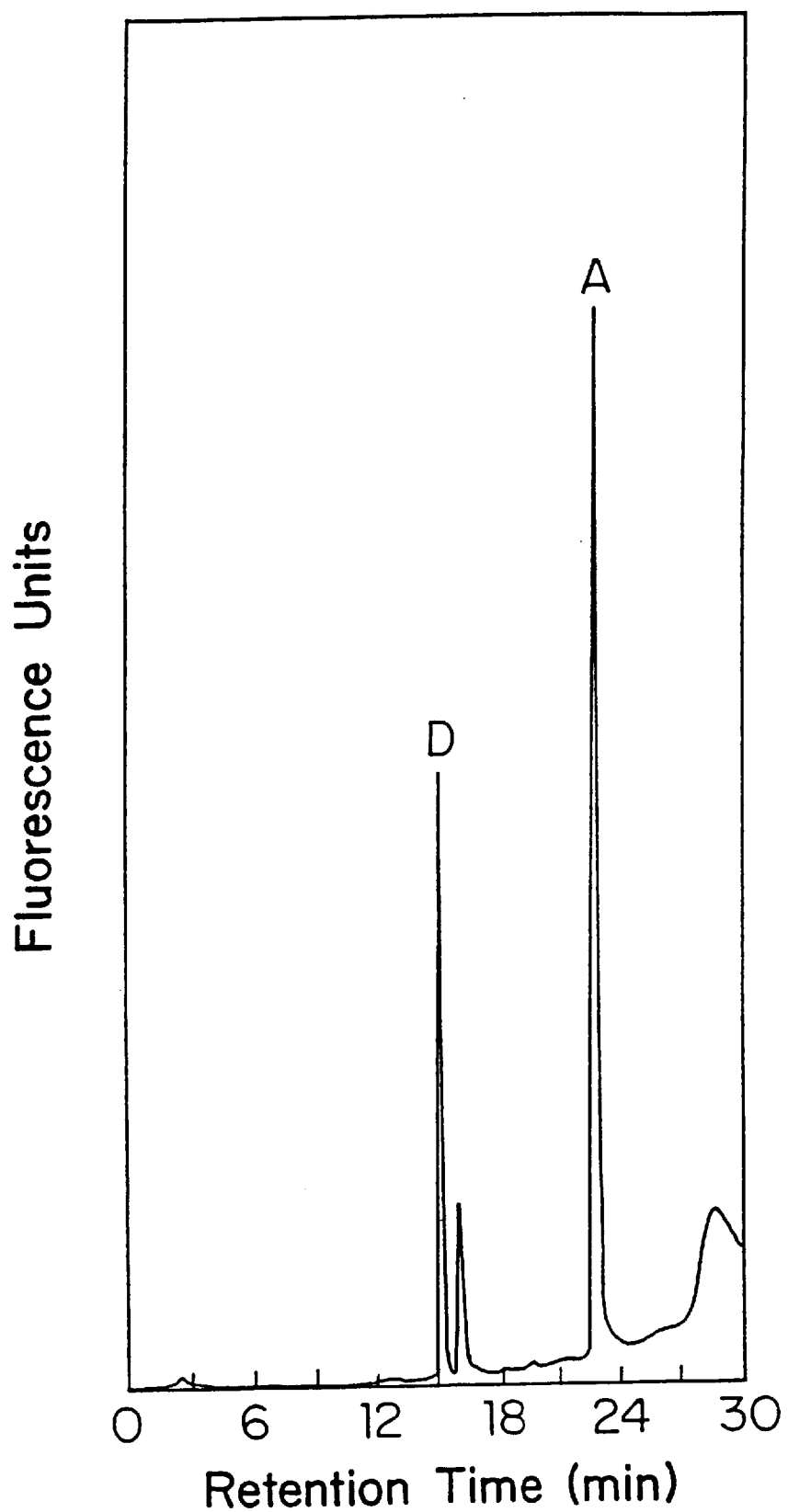
FIG. 13 depicts reverse phase HPLC analysis with fluorescence detection of the MTZ derivative of aspartate and alanine after reaction with dansyl ethylenediamine (Example IX).
Figure 14:
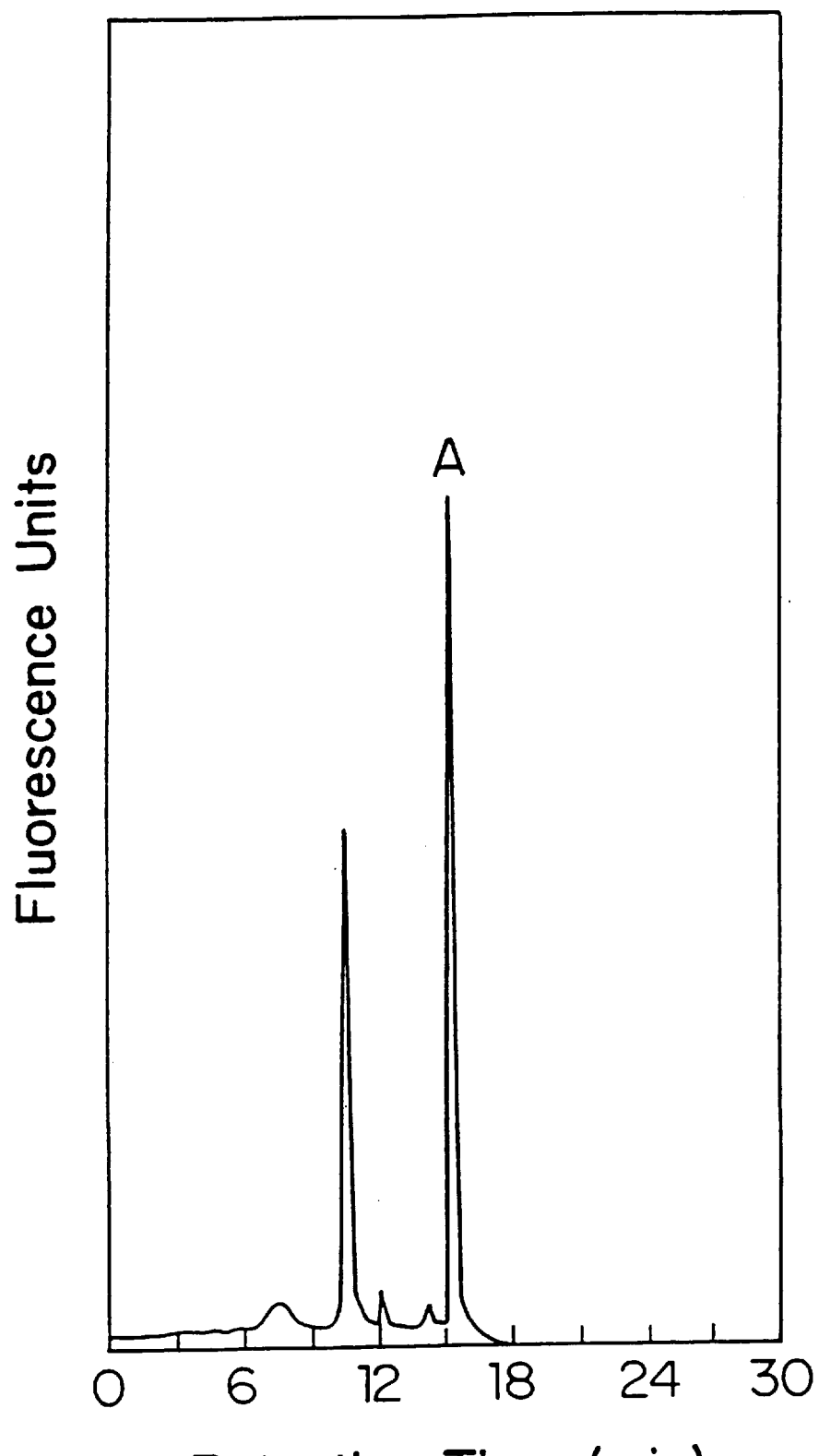
FIG. 14 depicts the reverse phase HPLC analysis with fluorescence detection of the MTZ derivative of alanine after reaction with 9-(aminomethyl)fluorescein (Example IX).

Reverse Phase HPLC With Fluorescence Detection of the MTZ Derivatives of Aspartate and Alanine After Reaction With Dansyl Ethylenediamine Reverse phase HPLC of the Methoxythiocarbonyl aspartate (dansyl ethyleneamine)amide (11.5 pmol) and Methoxythiocarbonyl alanine (dansyl ethyleneamine)amide (14 pmol) derivatives was performed on a C-18 (5μ, 300 Å) Reliasil column (2.0 mm×250 mm) on a Beckman 126 Pump Module with a Shimadzu (RF-535) Fluorescence detector. See FIG. 13. The column was eluted by a discontinuous gradient from solvent A (10 mM phosphoric acid, pH 7.0, in water containing 10% acetonitrile) to solvent B (10 mM phosphoric acid, pH 7.0, in water containing 50% n-propanol) at a flow rate of 0.25 ml/min at 35° C. The gradient used was as follows: 30% B for 4 minutes, 30–40% B over 30 minutes, 40–50% B over 15 minutes, 50–80% B over 6 minutes. Fluorescence excitation and emission were monitored at 334 nm and 520 nm, respectively. The range setting was at 8. FIG. 13 includes peak A (alanine) and D (aspartate).

EXAMPLE X

Reverse Phase HPLC With Fluorescence Detection of the MTZ Derivatives of Alanine After Reaction With 5-(Aminomethyl)fluorescein Reverse phase HPLC of the Methoxythiocarbonyl alanine (aminomethylfluorescein)amide (5 femtomol) derivative was performed on a C-18 (5$\mu$, 300 Å) Reliasil column (2.0 mm×250 mm) on a Beckman 126 Pump Module with a Shimadzu (RF-535) Fluorescence detector. The column was eluted by a linear gradient from solvent A (10 mM phosphoric acid, pH 8.0, in water containing 10% acetonitrile) to solvent B (10 mM phosphoric acid, pH 8.0, in water containing 50% n-propanol) at a flow rate of 0.25 ml/min at 35° C. The gradient used was as follows: 2% B for 4 minutes, 2–60% B over 30 minutes. Fluorescence excitation and emission were monitored at 491 nm and 516 nm, respectively. The range setting was at 16. The Reliasil columns were chosen for this work at pH 8.0 since these silica based columns are stable at these elevated pH's. Referring to FIG. 15, Peak A is methoxythiocarbonyl alanine (aminomethylfluorescein)amide (5-femtomole).

SUMMARY

1. This invention provides a new reagent for N-terminal sequencing that forms thiazolinone derivatives which can be quantitatively labeled with amine nucleophiles containing groups optimal for detection by either mass spectrometry or fluorescence.

2. Based on prior experience with detection of thiohydantoin derivatives containing the dimethylaminopropyl group by electrospray mass spectrometry (32), the anticipated level of sensitivity is expected to be approximately 20–50 femtomoles.

3. Based on fluorescent measurements of the amino acid derivatives formed in this study with 5-(aminomethyl) fluorescein, the sensitivity of detection by reverse phase HPLC with fluorescence detection (with a 2 mm I.D. column) is anticipated to be 1–5 femtomoles.

BIBLIOGRAPHY

1. Edman, P., *Acta Chem. Scand.* 4:283–293 (1950).
2. Edman, P., et al. *Eur. J. Biochem.* 1:80–91 (1967).
3. Hewick, R. M., et al., *J. Biol. Chem.* 256:7990–7997 (1981).
4. Waldron, et al., *Anal. Chem.* 64:1396–1399 (1992).
5. Chang, J. Y., et al., *Biochem. J.* 153:607–611 (1976).
6. Chang, J. Y., et al., *FEBS Lett.* 93:205–214 (1978).
7. Salnikow, J., et al., *Methods in Protein Sequence Analysis* (Ed. Elzinga, M.) Humana Press, Clifton, N.J., pp. 181–188 (1982).
8. Aebersold, R. H., et al., *Biochemistry* 27:6860–6867 (1988).
9. Aebersold, R. H., et al., *Methods in Protein Sequence Analysis* (Ed. Wittmann-Liebold, B.) Springer-Verlag, Berlin, pp. 79–97 (1989).
10. Maeda, H., et al., *Biochem. Biophys. Res. Commun.* 31:188–192 (1968).
11. Muramoto, K., et al., *Anal. Biochem.* 141:446–450 (1984).
12. Hirano, H., et al., *Biol. Chem. Hoppe-Seyler* 367:1259–1265 (1986).
13. Hirano, H., et al., *Methods in Protein Sequence Analysis* (Ed. Wittmann-Liebold, B.) Springer-Verlag, Berlin, pp. 42–51 (1989).
14. Jin, S. W., et al., *FEBS Lett.* 198:150–154 (1986).
15. Jin, S. W., et al., *Methods in Protein Sequence Analysis* (Ed. Wittmann-Liebold, B.) Springer-Verlag, Berlin, pp. 34–41 (1989).
16. Salnikow, Jr., et al., *Methods in Protein Sequence Analysis*-1986 (Ed. Walsh, K. A.) Humana Press, Clifton, N.J., pp. 247–260 (1987).
17. L'Italien, J. J., et al., *J. Chromatogr.* 283:149–156 (1984).
18. Inman, J. K., et al., *Methods Enzymol.* 47:374–385 (1977).
19. Tsugita, A., et al., *J. Biochem.* 103:399–401 (1988).
20. Horn, M. J., et al., *Techniques in Protein Chemistry* (Ed. Hugli, T. E.) Academic Press, San Diego, pp. 51–58 (1989).
21. Margolies, M. N., et al. *Methods in Protein Sequence Analysis* (I.Ed. Elzinga, M.) Humana Press, Clifton, N.J., pp. 189–203 (1982).
22. Tsugita, A., et al., *J. Biochem.* 106:60–65 (1989).
23. Pavlik, M., et al., *Anal. Biochem.* 201:9–16 (1992).
24. Simpson, R. J., et al., *Anal. Biochem.* 177:221–236 (1989).
25. Hugli, E. E., Ed., *Techniques in Protein Chemistry*, Academic Press, San Diego (1989).
26. L'Italien, J. J. Ed., *Proteins: Structure and Function*, Plenum Press, New York (1987).
27. Matsudaira, P. T. Ed. *A Practical Guide to Protein and Peptide Purification for Microsequencing*, Academic Press, San Diego (1989).
28. Shively, J. E. Ed. *Methods of Protein Mischaracterization*, Humana Press, Clifton, N.J. (1986).
29. Walsh, K. A. Ed., *Methods in Protein Sequence Analysis*-1986, Humana Press, Clifton, N.J. (1987).
30. Wittmann-Liebold, B. Ed., *Methods in Protein Sequence Analysis*, Springer-Verlag, Berlin (1989).
31. Merril, C. R., et al., *Science* 211:1437–1438 (1981).
32. Bailey, J. M., et al., *Techniques in Protein Chemistry V* (Crabb, J. W., Ed) pp. 169–178, Academic Press, Inc. (1994).
33. Farnsworth, et al., *Anal. Biochem.* 215:190–199 (1993).
34. Aebersold, R., et al. *Protein Science* 1:494–503 (1992).
35. U.S. Pat. No. 5,240,859.
36. Waidyanatha, S., et al., *39th ASMS Conference Proceedings*, pp. 1400–1401 (1991).
37. Stolowitz, M. L., et al., *Methods in Protein Sequence Analysis* (Imahori, K./Sakiyama, F., Eds.) pp. 37–44, Plenum Publishing Corp. (1993).
38. Kenner, G. W., et al. *J. Chem. Soc.,* 2076–2081 (1952).

I claim:

1. A process for the N-terminal degradation of a polypeptide which comprises:
   (i) reacting said polypeptide with an alkoxythiocarbonylimidazole to produce a thiourea derivative at the N-terminus of said polypeptide;
   (ii) reacting said derivative with acid to provide a thiazolinone derivative of the N-terminal amino acid of said polypeptide; and
   (iii) reacting said thiazolinone derivative with a reagent to provide a detectable compound.

2. The process of claim 1 in which said alkoxythiocarbonylimidazole in step (i) has the formula:

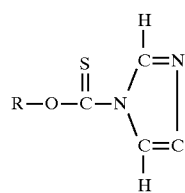

in which R is a straight or branched chain alkyl group having 1 to 8 carbon atoms or a phenyl group.

3. The process of claim 1 or claim 2 in which each of step (i) is conducted at a temperature of 25° C. to 70° C.

4. The process of claim 1 in which said alkoxythiocarbonylimidazole in step (i) is methoxythiocarbonylimidazole.

5. The process of claim 1 or claim 2 in which said acid in step (ii) is trifluoroacetic acid, hexafluorobutyric acid or hydrochloric acid.

6. The process of claim 1 or claim 2 in which said polypeptide in step (i), said thiourea derivative in step (ii) and said thiazolinone derivative in step (iii) are in solution in dimethylformamide, or acetonitrile or methanol.

7. The process of claim 1 or claim 2 in which said polypeptide in step (i) is attached to a support.

8. The process of claim 1 or claim 2 in which said polypeptide in step (i) and said alkoxycarbonylimidazole in step (i) are in solution in dimethylformamide, acetonitrile or methanol and in which said solution contains 100 picomoles to 5 nanomoles of said polypeptide and 0.5 micromoles to 100 millimoles of said alkoxythiocarbonylimidazole.

9. The process of claim 1 or claim 2 in which said reagent in step (iii) contains a fluorescent group or an ionizable group detectable by mass spectrometry.

10. The process of claim 1 or claim 2 in which said polypeptide contains 2 to 500 amino acid residues;

said alkoxythiocarbonylimidazole is methoxythiocarbonylimidazole; and said reagent to provide a detectable compound, provides a fluorescent group or an ionizable group detectable by mass spectrometry.

11. A process which comprises reacting a straight or branched chain alkanol having 1 to 8 carbon atoms or phenol with 1,1'thiocarbonyldiimidiazole to produce a compound having the formula:

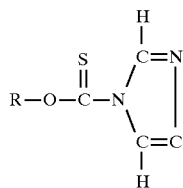

in which R is a straight or branched chain alkyl group having 1 to 8 carbon atoms or a phenyl group.

12. The claim 11 process in which said alkanol is methanol or ethanol or propanol or isopropanol.

13. The claim 11 or claim 12 process in which said reacting of an alkanol with 1,1'thiocarbonyldiimidiazole is conducted at 25° to 70°.

14. A process for the N-terminal degradation of a polypeptide which comprises:

(i) reacting said polypeptide with an alkoxythiocarbonylimidazole to produce an alkoxy thiourea derivative at the N-terminus of said polypeptide;

(ii) reacting said derivative with acid to provide a thiazolinone derivative of the N-terminal amino acid of said polypeptide;

(iii) extracting said thiazolinone derivative from the reaction mixture formed in step (ii);

(iv) reacting said extracted thiazolinone with a reagent having an ionizable group detectable by mass spectrometry.

15. The claim 14 process in which said step (iv) reagent having an ionizable group is dimethylaminopropyl amine.

16. The process of claim 1 or claim 2 in which said polypeptide in step (i) is non-covalently absorbed to a polyvinyldifluoride or polytetrafluoroethylene.

* * * * *